(12) United States Patent
Park et al.

(10) Patent No.: US 7,754,491 B2
(45) Date of Patent: Jul. 13, 2010

(54) SENSOR FOR MEASURING SYNGAS RATIOS UNDER HIGH TEMPERATURE AND PRESSURE CONDITIONS

(75) Inventors: Chan Seung Park, Yorba Linda, CA (US); Colin E. Hackett, Riverside, CA (US); Nora A. Hackett, legal representative, Riverside, CA (US); Joseph M. Norbeck, Riverside, CA (US)

(73) Assignee: The Regents of the University of Calif., Oakland, CA (US)

( * ) Notice: Subject to any disclaimer, the term of this patent is extended or adjusted under 35 U.S.C. 154(b) by 1149 days.

(21) Appl. No.: 11/299,030

(22) Filed: Dec. 9, 2005

(65) Prior Publication Data

US 2007/0131567 A1    Jun. 14, 2007

(51) Int. Cl.
*G01N 33/00* (2006.01)
*G01N 33/22* (2006.01)
*G01N 31/12* (2006.01)
*G01N 25/18* (2006.01)

(52) U.S. Cl. .................. 436/134; 436/144; 436/137; 422/78; 422/94; 422/95; 73/23.21; 73/23.31; 73/25.03

(58) Field of Classification Search .................. None
See application file for complete search history.

(56) References Cited

U.S. PATENT DOCUMENTS

| | | | |
|---|---|---|---|
| 2,888,330 A | 5/1959 | Kapff | |
| 3,957,460 A | 5/1976 | Lee | |
| 3,985,519 A | 10/1976 | Kalina et al. | |
| 4,005,001 A | 1/1977 | Pebler | |
| 4,012,311 A | 3/1977 | Greene | |
| 4,012,692 A | 3/1977 | Eicker | |

(Continued)

FOREIGN PATENT DOCUMENTS

| | | |
|---|---|---|
| EP | 0 952 132 A1 | 10/1999 |
| WO | WO03/066517 A1 | 8/2003 |

OTHER PUBLICATIONS

A.S.K. Raju, C.S. Park and J.M. Norbeck, Synthesis Gas Production using Steam Hydrogasification and Steam Reforming, Accepted, Fuel Proc. Tech., 2008.

(Continued)

*Primary Examiner*—Jill Warden
*Assistant Examiner*—Neil Turk
(74) *Attorney, Agent, or Firm*—Berliner & Associates

(57) ABSTRACT

An assembly and method for gas analysis. The assembly comprises a catalyst compartment for catalytically reacting a component of a gas sample, producing one or more gas species as products. A product compartment receives the gas species, and a sensing element within the compartment senses the amount of one or more of the gas species. This amount is compared to the amount of the same gas species present in a reference compartment containing a non-catalyzed gas sample, providing the amount of the gas species produced by catalysis. Using this value, the content of the gas component in the gas sample is calculated based upon the stoichiometry of the catalyzed reaction. In preferred embodiments, the gas for analysis is a process gas for fuel production, and the catalyst is a high temperature shift catalyst that catalyzes the reaction of carbon monoxide and water into hydrogen and carbon dioxide.

10 Claims, 2 Drawing Sheets

U.S. PATENT DOCUMENTS

| | | | |
|---|---|---|---|
| 4,073,698 | A | 2/1978 | Blurton et al. |
| 4,158,697 | A | 6/1979 | Cramer |
| 4,170,455 | A | 10/1979 | Henrie |
| 4,394,239 | A | 7/1983 | Kitzelmann et al. |
| 4,397,888 | A | 8/1983 | Yannopoulos et al. |
| 4,668,635 | A | 5/1987 | Forster |
| 4,822,935 | A | 4/1989 | Scott |
| 4,833,171 | A | 5/1989 | Sweeney |
| 4,983,296 | A | 1/1991 | McMahon et al. |
| 5,055,266 | A | 10/1991 | Stetter |
| 5,250,175 | A | 10/1993 | Des Ormeaus |
| 5,344,848 | A | 9/1994 | Steinberg et al. |
| 5,439,580 | A | 8/1995 | Akbar et al. |
| 5,447,559 | A | 9/1995 | Rao et al. |
| RE35,377 | E | 11/1996 | Steinbert et al. |
| 6,053,954 | A | 4/2000 | Anderson et al. |
| 6,225,358 | B1 | 5/2001 | Kennedy |
| 6,350,288 | B1 | 2/2002 | Hirayama et al. |
| 6,495,610 | B1 | 12/2002 | Brown |
| 6,527,980 | B1 | 3/2003 | Roden et al. |
| 6,612,269 | B2 | 9/2003 | Heffel et al. |
| 7,208,530 | B2 | 4/2007 | Norbeck et al. |
| RE40,419 | E | 7/2008 | Norbeck et al. |
| 2003/0022035 | A1 | 1/2003 | Galloway |
| 2005/0032920 | A1 | 2/2005 | Norbeck et al. |
| 2005/0165261 | A1 | 7/2005 | Abazzajiian et al. |
| 2005/0256212 | A1 | 11/2005 | Norbeck et al. |
| 2008/0021123 | A1 | 1/2008 | Norbeck et al. |

OTHER PUBLICATIONS

V.P. Natarajan and G.J. Supes, Rheological studies on a slurry biofuel to aid in evaluating its suitability as a fuel, Fuel, vol. 76, 1997, pp. 1527-1535.

G. Atesok, F. Boylu, A.A. Sirkeci and H. Dincer, The effect of coal properties on the viscosity of coal-water slurries, Fuel, vol. 81, 2002, pp. 1855-1858.

F. Boylu, H. Dincer and G. Atesok, Effect of coal particle size distribution, volume fraction and rank on the rheology of coal-water slurries, Fuel Proc. Tech., vol. 85, 2004, pp. 241-250.

N. V. Pimenova and T. R. Hanley, Measurement of rheological properties of corn stover susspensions, App. Biochem. and Biotech., vol. 105-108, 2003, pp. 383-392.

H. A. Barnes and Q. D. Nguyen, Rotating vane rheometry—a review, J. Non-Newtonian Fluid Mech. vol. 98, 2001, pp. 1-14.

N. I. Heywood, Stop you slurries from stirring up trouble, Chem. Engr Proc. vol. 95, 1999, pp. 21-40.

S. K. Majumder, K. Chandna, D. S. De and G. Kundu, Studies on flow characteristics of coal-oil-water slurry system, Int. J of Miner. Proc., vol. 79, 2006, pp. 217-224.

Ayhan Demirbas, Thermochemical Conversion of Biomass to Liquid Products in the Aqueous Medium, *Energy Sources*, 27:1235-1243, 2005.

Kreda, Silvia et al, G-protein-coupled receptors as targets for gene transfer vectors using natural small-molecular ligands, *Nature Biotechnology*, vol. 18 Jun. 2000.

Steynberg, A.; Dry, M., FT Technology Studies in surf Science and Catalysis, ec., vol. 152, 2005.

Sheldon, R.A. Chemicals from Synthesis Gas, 1983.

Van der Laan, G.P., Thesis, University of Groningen, Netherlands, 1999.

Olsen et al., Unit processes and principles of chemical enginnering, D.Van Nostrand Co., 1032, pp. 1-3, Jul. 5, 1932.

Hepola, Jouko et al, Sulphur poisoning of nickel-based hot gas cleaning catalysts in synthetic gasification gas I. Effect of different process parameters, *B. Environmental*, 14 (1997) 287-303.

Tomita, Akira, et al., Sulfur Poisoning in the Nickel Catalyzed Gasification of Activated Carbon in Hydrogen, *Carbon*, vol. 21, No. 3 pp. 225-229, 1983.

Sehested Jens, Four challenges for nickel steam-reforming catalysts, *catalysisToday*, 111 (2006) 103-110.

Chen, Ienwhei et al, Resistivity to Sulfur Poisoning of Nickel-Alumina Catalysts, *Ind. Eng. Chem. Res* 1988, 27, 1391-1396.

SENSOR FOR MEASURING SYNGAS RATIOS UNDER HIGH TEMPERATURE AND PRESSURE CONDITIONS

BACKGROUND

1. Field of Invention

This invention relates generally to gas sensors and methods of analyzing gases.

2. Related Art

Methods such as the Fischer-Tropsch process that produce synthetic liquid fuels from carbon monoxide and hydrogen mixtures require strict control of process parameters to efficiently produce the desired grades of fuel products. One of the most critical of these parameters is the ratio of hydrogen to carbon monoxide.

The majority of synthetic fuel production methods involve partial oxidation or steam reforming processes. These processes are usually performed at high pressure (about 500 psi) and high temperature (about 800° C.). Many of the analyzers for monitoring and control of the $H_2/CO$ ratio utilize sensors that operate at ambient temperature and pressure. As a result, cooling and pressure reduction devices must be installed between the process and the CO and $H_2$ analyzers. These devices add considerable complexity to the overall process and make the analyzer response times relatively slow. In addition, the analysis of $H_2$ and CO is often performed separately rather than by a single analyzer providing both gas measurements simultaneously.

Many current methods of CO analysis typically require the presence of oxygen to operate. In U.S. Pat. No. 4,073,698 to Blurton et al., a method is described based on the selective oxidation of hydrogen, which prevents this gas from interfering with the measurement of CO. In U.S. Pat. No. 4,394,239 to Kitzelmann et al., a method is described for measuring the concentration of CO and $H_2$ in ambient air. Another method, described in U.S. Pat. No. 4,397,888 to Yannopoulos et al., requires oxygen across a stannic oxide thick-film sensor that uses different dopants to distinguish between CO and $H_2$. A method described in U.S. Pat. No. 5,439,580 to Akbar et al. also requires gas-specific dopants to distinguish between CO and $H_2$.

The measurement of CO and $H_2$ in a process gas stream is a particular example of a gas measurement that could be carried out faster and more efficiently at elevated temperatures and pressures. There remains a need for continued development of devices and methods for high temperature and high pressure gas analysis.

SUMMARY

The present invention provides an assembly and a method for gas analysis that can be used at ambient conditions or under high temperature and high pressure conditions. In particular embodiments, the present invention provides close to real time analysis of a process gas stream.

In one aspect, the present invention provides a gas sensor assembly for monitoring a component of a gas. The assembly includes: a) a catalyst compartment, for receiving a sample of a gas and for holding a catalyst that catalyzes a chemical reaction involving a component of the gas whereby one or more gas species is produced; b) a product compartment in fluid communication with the catalyst compartment, for receiving some or all of the one or more gas species produced by catalysis; and c) a sensing element disposed within the product compartment, for sensing the amount of at least one gas species produced by catalysis, thereby providing a value for analyzing the amount of the gas component contained in the gas. The sensor assembly can further include: d) a reference compartment for receiving a second sample of the gas; and e) a second sensing element disposed within the reference compartment, for sensing the same gas species as sensed after catalysis, thereby providing a reference value for analyzing the amount of the gas component contained in the gas. In preferred embodiments, the gas sensor assembly also includes a catalyst for catalyzing the chemical reaction involving the gas component.

Two values can be determined, one value corresponding to the amount of the gas species contained in a gas product after catalysis, the other value corresponding to the amount of the gas species present in a gas sample before catalysis. The difference between these two values provides a measure of the amount of the gas species produced by catalysis. Using this measure, the content of the gas component of interest can be determined from the stoichiometry of the catalyzed chemical reaction. In essence, the gas component is analyzed by transforming it into a different gas species, whose content is then determined. The advantage of this transformation is that the resulting gas species can be more easily or conveniently detected. For example, in certain embodiments, CO in a process gas is catalytically reacted with $H_2O$ to produce $H_2$ and $CO_2$. The amount of $H_2$ can be determined by thermal conductivity analysis, and the CO content of the process gas can be calculated from the stoichiometry of the catalyzed reaction. The value corresponding to the amount of the gas species before catalysis can be determined separately from the gas sensor assembly, or can be determined in a reference compartment that is part of the gas sensor assembly.

In further embodiments, by choosing the appropriate chemical reaction and gas assembly setup, the ratio of various components of a gas can be determined directly from a monitor in close to real time analysis.

In another aspect, the present invention provides a method of monitoring a component of a gas. The method comprises: a) transferring a first sample of a gas to a first compartment of a gas sensor assembly; b) in the first compartment, catalyzing a chemical reaction involving a component of the gas, whereby one or more gas species is produced; c) transferring some or all the one or more gas species to a second compartment of the gas sensor assembly; d) in the second compartment, sensing the amount of at least one gas species produced by catalysis; e) transferring a second sample of the gas to a third compartment of the gas sensor assembly; f) in the third compartment, sensing the amount of the same gas species as sensed after catalysis; and g) comparing the amount of the gas species after catalysis to the amount of the same gas species in the second gas sample, thereby providing a measure of the amount of the gas component contained in the gas. The comparison provides a measure of the amount of the gas species produced by catalysis, which in turn is used to calculate the content of the gas component of interest. Thus, the amount of the gas species produced by catalysis provides a measure of the gas component of interest.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

Figure 1:
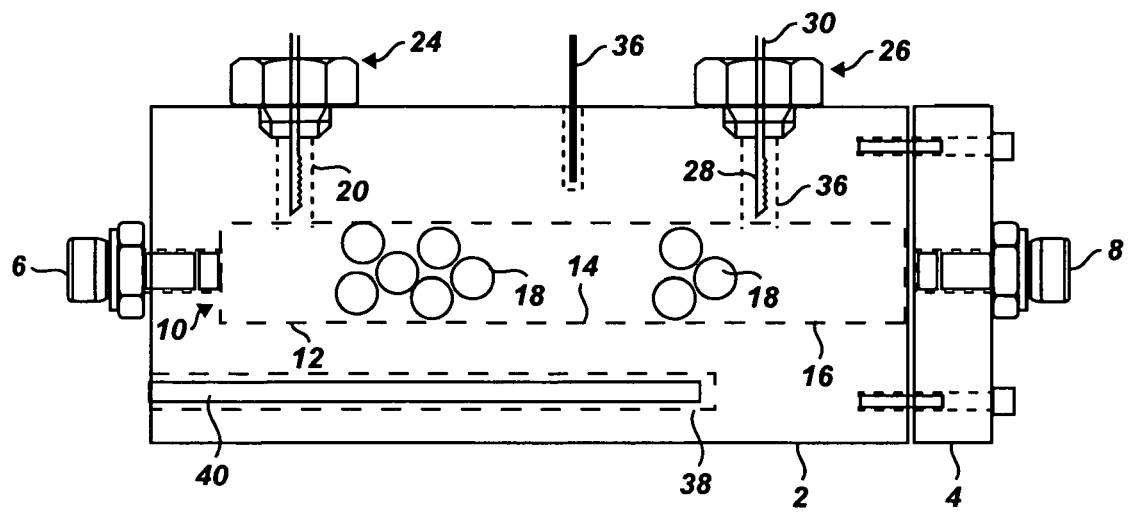
FIG. 1 is a schematic drawing of a gas sensor.

The present invention provides a gas sensor and a method of gas analysis. This invention was made with support from the City of Riverside, Calif. The City of Riverside has certain rights in this invention.

In accordance with the present invention, the gas for analysis can be any gas having a component capable of undergoing a catalyzed chemical reaction. The gas can comprise a single gas species or a mixture of two or more gas species. In particular embodiments, the gas is a gas stream such as a process gas stream for synthetic fuel production. Although the composition of the first sample of the gas and the second sample of the gas can be the same, the first and second gas samples can differ depending on the uniformity of the gas being analyzed. For example, when the gas is a process gas stream, the composition of the gas stream can differ due to fluctuations in gas production. Nonetheless, a comparison of the first and second gas samples provides a measure of the gas component of interest, particularly when the process gas is sampled at short time intervals.

The catalyst can be any substance that catalyzes a chemical reaction involving a gas component of interest so long as the catalyst does not prevent the detection of the particular gas species to be measured. Preferably, the catalyst is a solid that remains in the catalyst compartment throughout the course of gas component analysis. Examples of gas components and catalysts include, but are not limited to, selective catalytic reduction catalysts such as vanadium for $NH_3$ analysis, and carbon-based catalysts for $NO_2$ analysis. In preferred embodiments, the catalyst is a shift catalyst that catalyzes the following reaction, known as the shift reaction: $CO+H_2O \rightarrow H_2+CO_2$. Examples of shift catalysts include, but are not limited to, iron-chromium based high temperature shift catalysts, copper-zinc-aluminum based low temperature shift catalysts, and noble metal based medium temperature shift catalysts. A high temperature shift catalyst capable of catalyzing a shift reaction at temperatures of about 300° C. or higher are particularly preferred. Such high temperature shift catalysts are commercially available (KATALCO 71-5 from Johnson Matthey Inc., Wayne, Pa., USA ; HTS SK-201-2 from Haldor Topsoe Inc., Houston, Tex., USA).

For the most accurate measure of a gas component of interest, the catalyzed chemical reaction preferably is one that goes to completion, i.e., that is irreversible. In preferred embodiments, substantially all of the gas component is catalyzed. By "substantially all" is meant that the amount of the gas component remaining after catalysis is not more than 1% of the gas component present before catalysis. During data analysis, any error in measurement due to incomplete conversion of a gas component can be compensated for as long as the percent conversion remains relatively constant.

The sensing element can be any gas sensing device that can be used to determine the amount of a selected reaction product. Examples of sensing elements include, but are not limited to, thermal conductivity sensing elements, semi-conductor sensing elements, ceramic oxide based sensing elements, electro-chemical sensing elements, metal hydride based sensing elements, and infra-red sensing elements.

In preferred embodiments, the sensing element is a thermal conductivity sensing element. As is known, thermal conductivity is a bulk property of gases, and thermal conductivity sensing elements are considered to be non-specific gas sensing devices. A thermal conductivity sensing element is a resistance device such as a metal filament, metal film, thermistor, hotplate, carbon film, carbon composite, metal wound wire, metal single wire, conductive plastic, or other thermal conductivity sensing element. Particularly preferred are metal filament thermal conductivity sensing elements.

Certain gases, such as helium and hydrogen, have thermal conductivities that are much greater than the thermal conductivity of air, while other gases, such as nitrogen, argon, carbon dioxide, carbon monoxide, ammonia and nitrogen have thermal conductivities that are less than or similar to that of air. Thus, in a gas mixture containing hydrogen and carbon dioxide, for example, the thermal conductivity of the gas will be determined mainly by hydrogen.

In practice, gas analysis can occur at gas pressures up to about 500 psi and temperatures up to about 800° C. The gas pressure is preferably about 100 to 500 psi, more preferably about 200 psi to 500 psi, and even more preferably about 300 psi to 500 psi. Gas temperature is preferably about 100° C. to 800° C., more preferably about 200° C. to 800° C., even more preferably about 250° C. to 800° C. In preferred embodiments, gas analysis is carried out at about 300° C.

A schematic drawing of a sensor in accordance with the present invention is shown in FIG. 1. The sensor includes a sensor block 2, one side of which is connected to a cap 4. Gas is introduced into the sensor block via an inlet port connector 6, and exhausted through an outlet port connector 8. In this embodiment, both connectors are Swagelok connectors (Swagelock Company, Solon, Ohio, USA), although other connector fittings can be utilized. A sensor chamber 10 is divided into three sections or compartments: a reference compartment 12; a catalyst compartment 14; and a product compartment 16. A catalyst 18 is provided in the catalyst compartment. The reference, catalyst and product compartments can be arranged as continuous sections of a single sensor chamber, as shown in FIG. 1. Alternatively, each section can be physically separated from another section by a partition such as a diffusion baffle, or the compartments can be arranged as any combination of continuous and separated sections.

At the top of the sensor block are two cavities 20, 22 that provide gas sensing elements 24, 26 with access to the reference and product compartments, respectively. In this embodiment, the gas sensing elements are metal filament thermal conductivity sensing elements. The thermal conductivity sensing element 26 includes a metal filament 28 connected to signal wires 30. Also at the top of the sensor block is a temperature sensing element 36, which in this embodiment is a thermocouple, for measuring the temperature of the sensor block.

A cavity 38 at the bottom of the sensing block holds a heating element 40, which in this embodiment is a cartridge heater. The heating element 40 and the .temperature sensing element 36 are connected to a temperature controller to maintain the sensor block temperature at a desired value.

In operation, a test gas sample enters the reference compartment 12, then moves through the catalyst compartment 14 and into the product compartment 16. In the product compartment, the test gas sample is analyzed and compared to a reference gas sample that has entered the reference compartment 12 after the test gas sample. When the gas to be monitored is a gas flow, gas samples can continuously flow from the reference compartment, through the catalyst compartment, and into the product compartment for measurement. This provides for continuous monitoring of the gas flow. In a continuous flow environment, a gas sample has two functions. First, the gas sample enters the reference compartment 12 and acts as a reference gas sample for gas species present in the product compartment 16. Second, the gas sample undergoes catalysis in the catalyst compartment and enters the product compartment, where it is then analyzed. Thus, each gas sample acts as both a reference gas sample and a test gas sample for the gas sensor.

Gas species data can be captured and analyzed by a monitor electrically connected to the gas sensing elements. In the case of the gas sensor shown in FIG. 1, the gas sensing elements 24, 26 (metal filament thermal conductivity elements) can be connected to a Wheatstone bridge circuit such that the two sensors form two legs of the bridge circuit. An instrumentation amplifier can be connected to the bridge circuit to detect bridge circuit imbalance. The output of the instrumentation amplifier can be connected to a monitor to display the signal of the amplifier. When the catalyzed reaction is a shift reaction involving the catalysis of CO and $H_2O$ to produce $H_2$ and $CO_2$, the amplifier signal can represent the $H_2$ to CO ratio of the gas. Thus, the ratio of $H_2$ to CO can be determined directly from the bridge circuit without the need to calculate the stoichiometry of the catalyzed reaction. The monitor can also act as a temperature controller for maintaining sensor block temperature.

Figure 2:
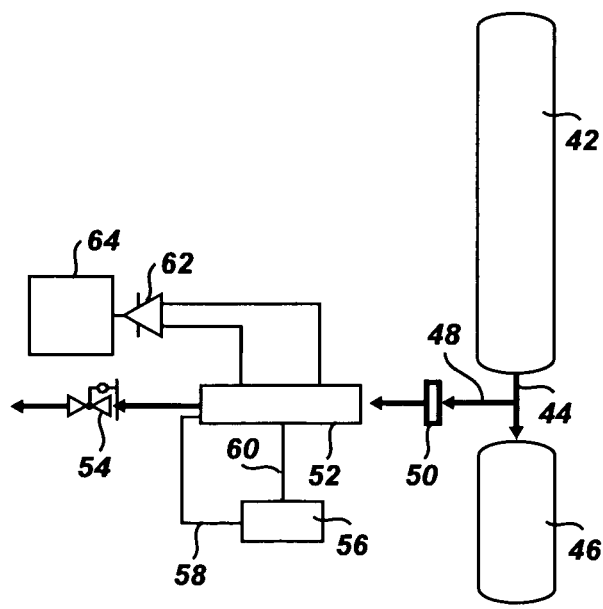
FIG. 2 is a block diagram of a process gas flow analysis.

A block diagram utilizing a sensor in accordance with the present invention is provided in FIG. 2. A steam methane reformer 42 converts steam and methane into carbon monoxide, hydrogen and residual steam, which form the producer gas stream 44 for a Fischer-Tropsch reactor 46. A process gas sample 48 is split off from the producer gas stream 44 and passed through an orifice 50 before entering a sensor block 52. The orifice limits the flow of gas into the sensor. A preferred rate of gas flow is about 5 sccm (standard cubic centimeter per minute). Other gas flow control devices can be substituted for the orifice including, but not limited to, a capillary flow control device or a needle valve. The gas sample is exhausted and vented from the sensor block following catalysis. A back pressure regulator 54 is used to maintain the pressure inside the sensor block at any desired pressure.

In FIG. 2, the temperature of the sensor block is maintained by connecting a temperature controller 56 to a thermocouple and a heating element attached to the sensor block. Connections are made via a heating element wire 58 and a thermocouple wire 60.

In the sensor block, one gas sample is sensed at a location corresponding to a reference compartment, and a second gas sample is sensed simultaneously at another location corresponding to a product compartment. Each location has a gas sensing element, in this case a metal filament thermal conductivity sensing element. Each thermal conductivity sensing element connects to a Wheatstone bridge amplifier 62 which in turn interfaces to a computer 64. When the thermal conductivity sensing elements form two legs of a Wheatstone bridge circuit, which measures the difference in resistance between the sensing elements, the imbalance in the bridge circuit will directly reflect the thermal conductivities of the gas samples in the reference and product compartments.

In other embodiments, a single gas sample provides both the test gas sample as well as the reference value for the test gas sample itself. In these embodiments, a gas sample first enters the reference compartment 12, where it is sensed. The gas sample then flows through the catalyst compartment 14 and into the product compartment 16, where sensing again occurs. A monitor compares the sensed value from the reference compartment to the sensed value from the product compartment, providing a measure of the amount of the gas component of interest. In this case, the monitor alternately compares the sensed values from the reference and product compartments rather than simultaneously comparing both compartments as is the case when two different gas samples provide the test gas sample and the reference gas sample, respectively.

Although the sensor assembly shown in FIG. 1 contains a single sensor chamber having catalyst, reference and product compartments, it will be understood that various components of the sensor assembly can be provided as separate units without altering the functioning of the assembly. For example, in some embodiments, the catalyst, reference and product compartments (with their respective sensing elements) can be separate chambers connected by gas-transporting conduits such as rigid or flexible tubing. In such embodiments, the reference and product compartments can be placed into an incubator at a selected temperature, while the catalyst compartment can be outside the incubator. In further embodiments, the catalyst and product compartments can be fluidly connected together, while the reference compartment is fluidly isolated from the catalyst and product compartments. In still further embodiments, a single chamber contains both the catalyst and product compartments, while a separate chamber contains the reference compartment.

In particular circumstances, the gas for analysis may not contain enough of the reactants necessary for catalysis. For example, water may be absent or may be present at too low a concentration to effectively carry out a shift reaction. In these situations, the necessary reactant(s) can be added to a gas sample prior to analysis.

The present invention may be better understood by referring to the accompanying examples, which are intended for illustration purposes only and should not in any sense be construed as limiting the scope of the invention as defined in the claims appended hereto.

EXAMPLE 1

A gas sensor in accordance with the sensor shown in FIG. 1 was constructed using a sensor block and a cap made of Aluminum 6061. The cap was attached to the sensor block by ¼ inch hex nuts and a silicon gasket. Tungsten filaments from GOW-MAC Instrument Co. (Bethlehem, Pa., USA) were used as thermal conductivity gas sensing elements in the reference and product compartments. A cartridge heater from Omega, Inc. (Stamford, Conn., USA) was inserted into the sensor block to maintain temperature, and a Type K thermocouple was connected to the sensor block for temperature measurement. In accordance with FIG. 1, the sensor block was about 1.5 inches high, about 3.0 inches long, and about 1.5 inches deep. The reference, catalyst and products compartments together were about 2.5 inches in length. The chamber containing the reference, catalyst and product compartments was about ½ inch in diameter.

EXAMPLE 2

The CO content of a gas containing carbon monoxide, hydrogen and water (steam) was determined. A high temperature shift catalyst, HTS SK-201-2 obtained from Haldor Topsoe Inc. (Houston, Tex., USA) was added to the catalyst compartment of a gas sensor constructed according to Example 1. The catalyst was disc-shaped (6 mm height, 6 mm diameter) and made of iron, chromium and copper oxide. The total weight of the catalyst in the catalyst compartment was about 5.5 grams. The gas sensor was connected to a Wheatstone bridge circuit such that the two tungsten filament thermal conductivity elements formed two legs of a bridge circuit. The bridge circuit measured the difference in resistance between the filaments. When the circuit was excited by current, either DC or AC, the imbalance in the bridge circuit reflected the thermal conductivity of the gas in the product and reference compartments.

The high temperature shift catalyst catalyzes the conversion of carbon monoxide and water into hydrogen and carbon dioxide as follows: $CO+H_2O \rightarrow H_2+CO_2$. With the catalyst used, the reaction time to completion was negligible. A gas sample introduced into the reference compartment flowed into the catalyst compartment, where the shift reaction occurred. The catalyzed gas sample then flowed into the product compartment, for analysis. A second gas sample was introduced into the reference compartment, providing a reference value for the catalyzed gas sample. The temperature of the sensor block was maintained at about 300° C.

Although thermal conductivity is a bulk property of a gas, the thermal conductivity of hydrogen is much greater than that of other gases. Therefore, the tungsten filament thermal conductivity elements essentially detect the hydrogen gas present in the first and second gas samples. The difference between the hydrogen gas in the first sample after catalysis and the hydrogen gas in the second sample before catalysis represents the amount of hydrogen produced by catalysis. Based on the stoichiometry of the shift reaction, this amount is also a measure of the amount of carbon monoxide present in the gas sample before catalysis. Therefore, measuring the amount of hydrogen produced gives a value for the CO content of the original gas.

Figure 3:
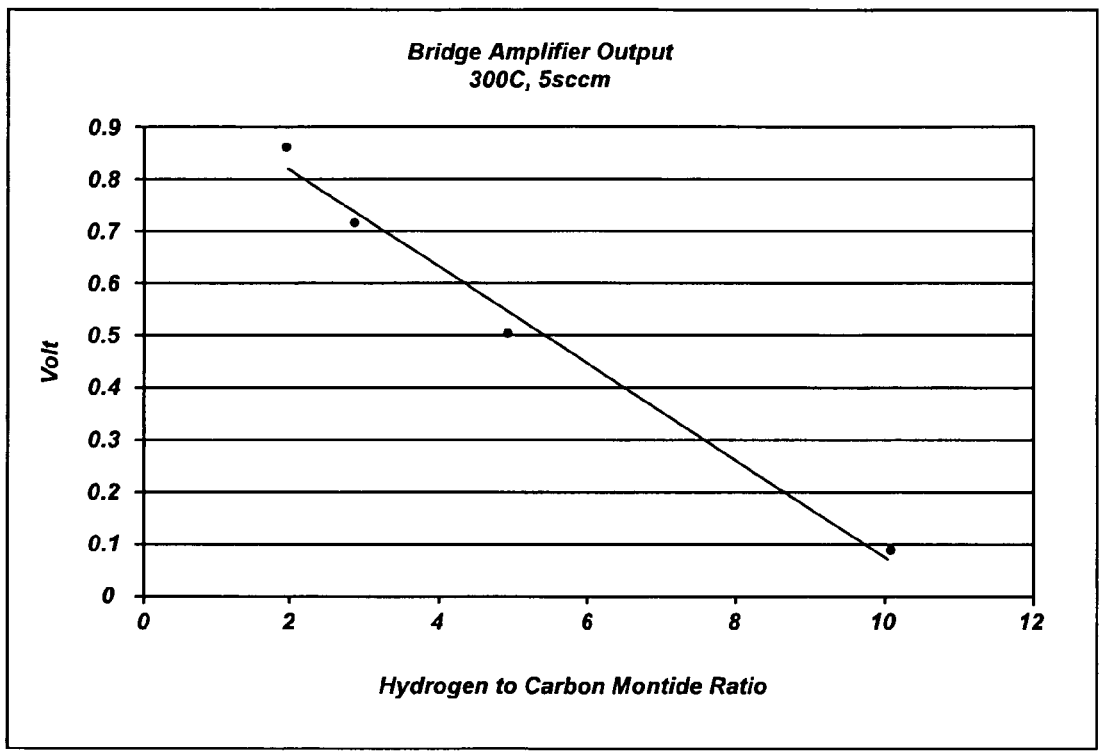
FIG. 3 is a graph showing the ratio of hydrogen to carbon monoxide as a function of bridge output.

The $H_2/CO$ ratio can be calculated from the values obtained from the gas sample measurements. However, by connecting the tungsten filaments of the reference and product compartments to two legs of a Wheatstone bridge circuit, the output signal from the bridge circuit directly indicates the $H_2/CO$ ratio. This is shown in FIG. 3, where gas samples containing different concentrations of carbon monoxide to hydrogen were analyzed.

Although the present invention and its advantages have been described in detail, it should be understood that various changes, substitutions and alterations can be made herein without departing from the spirit and scope of the invention. Moreover, the scope of the present application is not intended to be limited to the particular embodiments of the process, manufacture, composition of matter, means, methods and/or steps described in the specification. As one of ordinary skill in the art will readily appreciate from the disclosure of the present invention, processes, manufacture, compositions of matter, means, methods, or steps, presently existing or later to be developed that perform substantially the same function or achieve substantially the same result as the corresponding embodiments described herein may be utilized according to the present invention. Accordingly, the invention is intended to include within its scope such processes, manufacture, compositions of matter, means, methods, or steps.

What is claimed is:

1. A method of monitoring a component of a gas, comprising:
    a) transferring a first sample of a gas to a catalytic compartment of a gas sensor assembly;
    b) in the catalytic compartment, catalyzing a chemical reaction involving a component of the gas, whereby one or more gas species is produced;
    c) transferring some or all the one or more gas species to a product compartment of the gas sensor assembly;
    d) in the product compartment, sensing the amount of at least one gas species produced by catalysis;
    e) transferring a second sample of the gas to a reference compartment of the gas sensor assembly;
    f) in the reference compartment, sensing the amount of the same gas species as sensed in step (d); and
    g) determining a difference between the amount of the gas species produced by catalysis in step (d) to the amount of the same gas species in the second sample of the gas in step (f), thereby providing a measure of the amount of the gas component contained in the gas before catalysis, based on said difference and stoichiometry of said chemical reaction.

2. The method of claim 1, wherein the catalyzed chemical reaction is an irreversible reaction.

3. The method of claim 1, wherein substantially all of the gas component is catalyzed.

4. The method of claim 1, wherein the catalyzed chemical reaction is a shift reaction.

5. The method of claim 1, wherein the gas is a process gas stream for synthetic fuel production.

6. The method of claim 1, wherein the component of the gas is carbon monoxide.

7. The method of claim 1, wherein at least one of the gas species produced by catalysis is hydrogen.

8. A method of monitoring carbon monoxide in a gas, comprising:
    a) transferring a first sample of a gas to a catalytic compartment of a gas sensor assembly;
    b) in the catalytic compartment, catalyzing a shift reaction involving carbon monoxide in the first gas sample whereby hydrogen is produced;
    c) transferring some or all of the hydrogen produced by catalysis to a product compartment in the gas sensor assembly;
    d) in the product compartment, sensing the amount of hydrogen produced by catalysis;
    e) transferring a second sample of the gas to a reference compartment of the gas sensor assembly;
    f) in the reference compartment, sensing the amount of hydrogen contained in the second sample of the gas; and
    g) determining a difference between the amount of hydrogen produced by catalysis in step (d) to the amount of hydrogen in the second sample of the gas in step (f), thereby providing a measure of the amount of carbon monoxide contained in the gas before catalysis, based on said difference and stoichiometry of said shift reaction.

9. A method of monitoring a component of a gas, wherein the gas component is subject to a catalyzed chemical reaction that produces one or more gas species, the method comprising:
    a) providing a sample of the gas to a first compartment;
    b) in the first compartment, sensing the amount of at least one gas species to be produced by catalysis, thereby providing a reference value for the amount of the gas species contained in the gas sample before catalysis;
    c) transferring some or all of the gas sample to a second compartment of the gas sensor assembly;
    d) in the second compartment, catalyzing the chemical reaction that produces the one or more gas species;
    e) transferring some or all of the one or more gas species produced by catalysis to a third compartment of the gas sensor assembly;
    f) in the third compartment, sensing the amount of the same gas species as sensed in the gas sample before catalysis; and
    g) determining a difference between the amount of the gas species after catalysis to the amount of the same gas species contained in the gas sample before catalysis, thereby providing a measure of the amount of the gas component contained in the gas based on said difference and stoichiometry of said chemical reaction.

10. The method of claim 1, wherein the first and second sample of the gas can be the same or different.

* * * * *